US008486022B2

(12) United States Patent
Ludwig et al.

(10) Patent No.: US 8,486,022 B2
(45) Date of Patent: Jul. 16, 2013

(54) NEEDLE CATHETER WITH AN ANGLED DISTAL TIP LUMEN

(75) Inventors: Florian N. Ludwig, Mountain View, CA (US); Shubhayu Basu, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 874 days.

(21) Appl. No.: 12/167,791

(22) Filed: Jul. 3, 2008

(65) Prior Publication Data
US 2010/0004627 A1    Jan. 7, 2010

(51) Int. Cl.
*A61M 5/178*    (2006.01)

(52) U.S. Cl.
USPC ............. 604/164.01; 604/164.13; 604/272; 604/264; 604/508

(58) Field of Classification Search
USPC ............ 604/192–198, 272, 164.01, 164.13, 604/264, 508
See application file for complete search history.

(56) References Cited

U.S. PATENT DOCUMENTS

| | | | | |
|---|---|---|---|---|
| 4,935,025 A * | 6/1990 | Bundy et al. | | 606/180 |
| 5,419,777 A | 5/1995 | Hofling | | |
| 5,460,614 A * | 10/1995 | Castaneda | | 604/164.13 |
| 5,971,968 A | 10/1999 | Tu et al. | | |
| 6,090,130 A * | 7/2000 | Nash et al. | | 606/213 |
| 6,283,947 B1 | 9/2001 | Mirzaee | | |
| 6,302,870 B1 | 10/2001 | Jacobsen et al. | | |
| 6,346,099 B1 * | 2/2002 | Altman | | 604/528 |
| 6,478,769 B1 * | 11/2002 | Parker | | 604/66 |
| 6,485,475 B1 * | 11/2002 | Chelly | | 604/264 |
| 6,554,801 B1 | 4/2003 | Steward et al. | | |
| 6,585,716 B2 | 7/2003 | Altman | | |
| 6,613,026 B1 | 9/2003 | Palasis et al. | | |
| 6,623,473 B1 | 9/2003 | Ponzi | | |
| 6,689,086 B1 | 2/2004 | Nita et al. | | |
| 6,723,082 B1 | 4/2004 | Payne et al. | | |
| 6,944,490 B1 | 9/2005 | Chow | | |
| 6,997,903 B2 | 2/2006 | Wijay et al. | | |
| 7,094,209 B2 * | 8/2006 | Egnelov et al. | | 600/585 |
| 7,094,230 B2 | 8/2006 | Flaherty et al. | | |

(Continued)

FOREIGN PATENT DOCUMENTS

DE    102005044468 A1    3/2007
EP    0637436 A1    2/1995

(Continued)

OTHER PUBLICATIONS

"Eccentric." Merriam-Webster Online Dictionary. 2009. Merriam-Webster Online. Mar. 23, 2009 <http://www.merriam-webster.com/dictionary/eccentric>.*

(Continued)

*Primary Examiner* — Kevin C Sirmons
*Assistant Examiner* — Edelmira Bosques
(74) *Attorney, Agent, or Firm* — Fulwider Patton LLP

(57) ABSTRACT

A needle catheter configured for injecting an agent into a wall of a patient's body cavity, which directs a needle from the distal tip of the catheter into the wall of the body cavity at an angle relative to the axis of the shaft. The resulting angled injection pathway improves the retention of the agent in the body cavity wall, while keeping a distal section of the catheter substantially perpendicular to the body cavity wall for optimal push against the tissue at the injection site.

17 Claims, 3 Drawing Sheets

U.S. PATENT DOCUMENTS

| | | |
|---|---|---|
| 7,141,041 B2 | 11/2006 | Seward |
| 7,147,633 B2 | 12/2006 | Chee et al. |
| 7,150,738 B2 | 12/2006 | Ray et al. |
| 7,172,576 B2 | 2/2007 | Sawa et al. |
| 7,182,757 B2 * | 2/2007 | Miyata et al. ................ 604/528 |
| 7,187,971 B2 | 3/2007 | Sommer et al. |
| 2004/0030286 A1 * | 2/2004 | Altman ..................... 604/96.01 |
| 2005/0070844 A1 * | 3/2005 | Chow et al. ................ 604/95.04 |
| 2006/0064062 A1 * | 3/2006 | Gurusamy et al. ....... 604/170.03 |
| 2006/0106338 A1 | 5/2006 | Chang |

FOREIGN PATENT DOCUMENTS

| | | |
|---|---|---|
| WO | 9210142 A1 | 6/1992 |
| WO | 9404220 A1 | 3/1994 |
| WO | 9913785 A1 | 3/1999 |

OTHER PUBLICATIONS

The International Search Report dated Oct. 5, 2009 issued by the European Patent Office in the corresponding International Application No. PCT/US2009/047833.

* cited by examiner

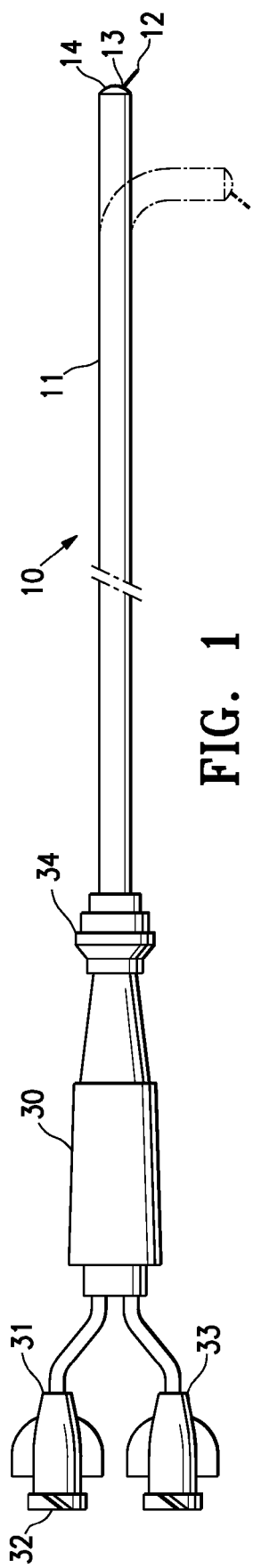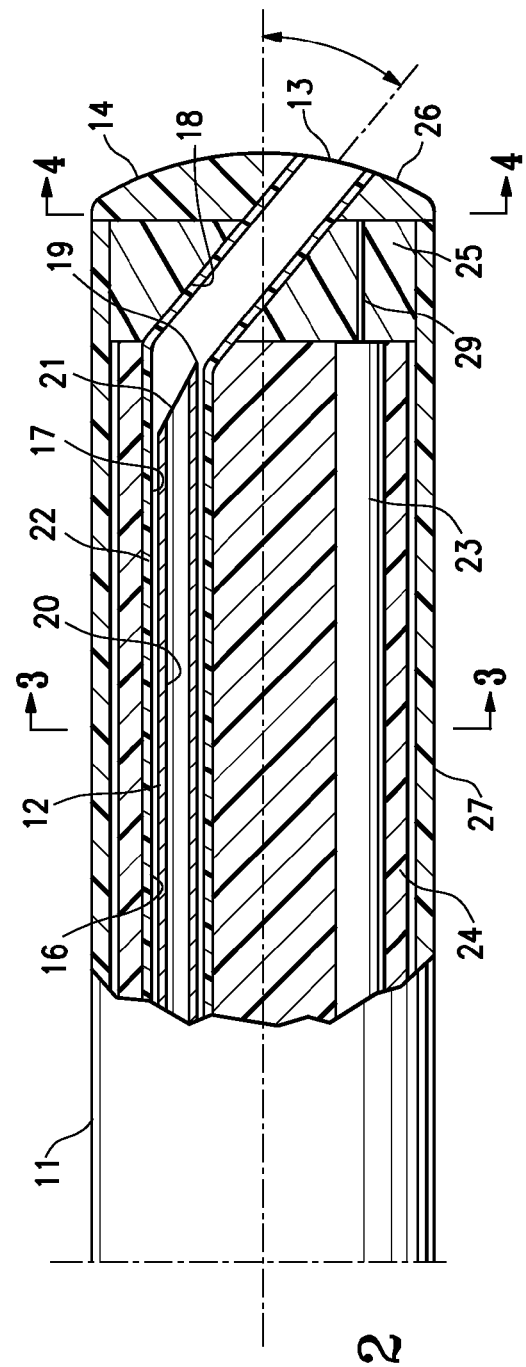
FIG. 1
FIG. 2

NEEDLE CATHETER WITH AN ANGLED DISTAL TIP LUMEN

CROSS-REFERENCES TO RELATED APPLICATIONS

None.

BACKGROUND OF THE INVENTION

The invention relates generally to the field of medical devices, and more particularly to a catheter used to deliver an agent to a patient's anatomy for the treatment or diagnosis of heart disease.

In the treatment of heart disease, a number of methods have been proposed in which a catheter or other therapeutic device is inserted into a chamber of the heart, and an operative distal end component of the device is used to perform the procedure on the inner wall of the heart. For example, agent delivery catheters, typically having deflectable distal sections, are configured for advancing in the patient's vasculature and into the heart chamber, and an agent delivered directly into the heart wall by jetting or needle-injecting it from the distal tip of the catheter. However, the beating heart can make it difficult to accurately place and maintain the operative distal end of the device at the desired treatment site. As a result, one difficulty has been providing a catheter that accurately delivers the agent to the desired site in a patient's heart chamber. Additionally, once delivered, truly effective treatment requires that the agent is retained at the treatment site for a certain minimum duration. In particular, it would be a significant advance to provide a catheter configured for targeted delivery of gene therapy and other therapeutic agents delivered into the heart wall (e.g., to the myocardium), or pericardial sac (by piercing the endocardium, myocardium, and epicardium) in a manner that improves agent retention.

SUMMARY OF THE INVENTION

The invention is directed to a needle catheter configured for injecting an agent into a wall of a patient's body cavity, which directs a needle from the distal tip of the catheter into the wall of the body cavity at an angle relative to the axis of the shaft. The resulting angled injection pathway improves the retention of the agent in the body cavity wall, while keeping a distal section of the catheter substantially perpendicular to the body cavity wall for optimal push against the tissue at the injection site.

A needle catheter of the invention generally comprises an elongated catheter shaft having a proximal end, a distal end, and a needle-through lumen therein which extends from the proximal end to a needle-through port in the distal end face of the catheter (i.e., the distal-most leading surface of the catheter) and which has an angled distal portion extending to the needle-through port at an angle greater than 0 degrees and less than 90 degrees relative to the longitudinal axis, and a hollow needle slidably disposed in the needle-through lumen of the shaft having a piercing distal tip and a lumen in fluid communication with a port in the piercing distal tip. The distal end face and the port of the needle-through lumen are configured to be pushed against the wall of the patient's body cavity. The needle has a retracted configuration in which the piercing distal tip of the needle is in the needle-through lumen of the shaft, and an extended configuration in which the piercing distal tip extends distally out the needle-through port, such that the catheter is configured to form an angled injection pathway in the wall of the patient's body cavity by directing the needle into the wall of the patient's body cavity at the angle of the angled distal portion of the needle-through lumen with the distal end face of the catheter pushed against the wall of the patient's body cavity at the injection site. In a presently preferred embodiment, the catheter has a deflectable distal section, and a handle on the proximal end of the catheter shaft is configured to effect catheter distal tip deflection and needle advancement and retraction.

A method of the invention includes introducing and advancing a needle catheter of the invention within a patient's body lumen such as the patient's vasculature, with the needle in a retracted configuration, to position the distal end of the catheter in the patient's body cavity, and pushing the distal end face, and preferably the needle-through port, against the patient's body cavity wall at a desired injection site, and advancing the needle to an extended configuration in which the piercing distal tip of the needle extends distally out the needle-through port, such that the needle extends into the body cavity wall at the angle of an angled distal portion of the needle-through lumen and thereby forms an angled injection pathway in the patient's body cavity wall. Agent from an agent source in fluid communication with the proximal end of the needle is then caused to flow through the needle lumen, to thereby deliver the agent into the angled injection pathway in the patient's body cavity wall. In a presently preferred embodiment, the patient's body cavity is a chamber of the heart, such as the left ventricle, and the agent is a therapeutic agent for treatment of heart disease and in particular heart failure. However, a variety of suitable agents can be used including diagnostic agents in a variety of suitable anatomical locations in the patient.

The angled injection pathway in the tissue, which results from the angled distal portion of the catheter needle-through lumen, preferably improves agent retention time. For example, compared to a needle extended straight into the heart tissue (i.e., in a direction normal to the surface of the tissue), the angled injection pathway preferably prevents or reduces the tendency of agent injected into the heart tissue to be expelled from injection pathway. Additionally, the angle preferably provides improved stabilization of the needle catheter which facilitates keeping the distal end face pushed against the beating heart wall during extension of the needle and infusion of the agent into the wall. Moreover, the catheter of the invention is configured to have excellent maneuverability and pushability (transmission of push force from the proximal end of the shaft) for positioning the distal end of the catheter at a desired injection site. These and other advantages of the invention will become more apparent from the following Detailed Description and accompanying exemplary drawings.

BRIEF DESCRIPTION OF THE DRAWINGS

FIG. 1 is an elevational view of a needle catheter embodying features of the invention, with the catheter needle illustrated in an extended configuration and deflection of a distal shaft section illustrated in broken line.

FIG. 2 is an enlarged view, partially in longitudinal cross section, of the distal shaft section of the catheter of FIG. 1, with the catheter needle illustrated in a retracted configuration.

DETAILED DESCRIPTION OF THE PREFERRED EMBODIMENTS

Figure 4:
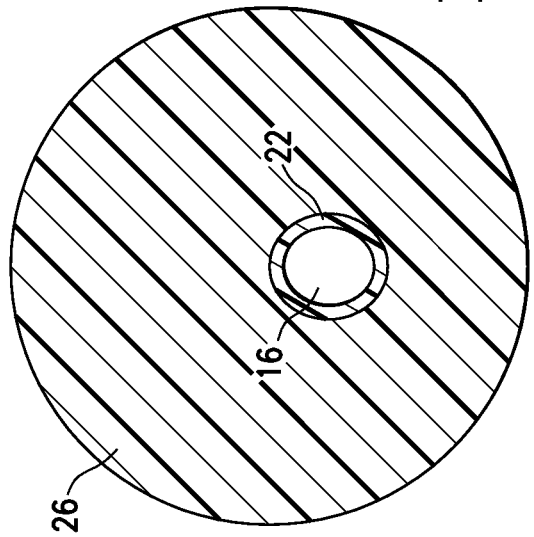
FIGS. 3 and 4 are transverse cross sectional views of FIG. 2, taken along lines 3-3 and 4-4.

FIG. 1 illustrates an elevational view of an agent delivery needle catheter 10 embodying features of the invention, generally comprising an elongated catheter shaft 11 having a proximal end and a distal end, and a needle 12 which is slidably disposed in the shaft and which has a retracted configuration, and an extended configuration in which the needle extends from a needle-through port 13 in a distal end face 14 of the catheter. In a presently preferred embodiment, the catheter 10 is configured for reversibly deflecting a distal shaft section, and FIG. 1 illustrates the catheter shaft 11 in a relaxed configuration for introducing and advancing within a patient's vasculature, and illustrates the deflected distal section of the catheter 10 in broken line. The needle 12 is illustrated extended from the catheter shaft in FIG. 1, although is should be understood that the needle is retracted into the shaft during introduction and positioning of the catheter 10 in the patient's anatomy.

FIG. 2 illustrates an enlarged view of the distal shaft section of the catheter 10, partially in longitudinal cross section. The catheter shaft has a needle-through lumen 16 therein extending from the proximal end of the shaft 11 to the needle-through port 13 in the distal end face 14 of the catheter. Preferably, the needle-through lumen is the single lumen of the shaft open to outside of the catheter in the distal shaft section, and the needle-through port is the single port in the distal tip section of the shaft. In the embodiment of FIG. 2, the needle-through lumen has an axially aligned portion 17 and an angled portion 18 which is distal to the axially aligned portion and which extends to the needle-through port 13 at an angle relative to the longitudinal axis of the shaft (shown in dashed line in FIG. 2). The hollow needle 12 is slidably disposed in the needle-through lumen 16 of the shaft 11, and has a piercing distal tip 19 and a lumen 20 in fluid communication with a port 21 in the piercing distal tip, such that the catheter is configured to form an angled injection pathway in the wall of the patient's body cavity by directing the needle 12 into the wall of the patient's body cavity at the angle of the angled distal portion 18 of the needle-through lumen with the distal end face 14 against the wall of the patient's body cavity at the injection site. The location of the lumen bend at the junction between the axially aligned portion 17 and the angled portion of the needle-through lumen 16 depends on factors such as the angle of the bend, but is also designed to facilitate sliding the needle 12 in the needle-through lumen 16 to the tissue-contacting port 13 of the distal end face 14. In the embodiment illustrated in FIG. 2, the lumen bend is abrupt (short), in that the angled section directly intersects the axially aligned section of the lumen 16. However, the needle-through lumen 16 may alternatively transition from the axially aligned portion 17 to the angled portion 18 through the shape of a more gentle curve. Additionally, in an alternative embodiment, the needle-through lumen 16 extends, at least in part, helically to the needle-through port 13 as discussed in more detail below, to direct the needle 12 to exit from the catheter at an angle. The angled portion 18 typically extends across the longitudinal axis of the shaft. As a result, the needle-through port 13 is typically eccentrically located in distal end face 14 of the shaft, although depending on the angle and length of the angled portion 18, the port 13 could alternatively be located coaxially in the center of the face 14.

The length and angle of the angled portion 18 and the curvature of the distal tip are preferably configured to facilitate positioning the needle-through port 13 against the wall of the patient's body cavity (i.e., the port 13 is located in a surface configured to be a tissue-contacting surface of the catheter during agent infusion). The proximal end of the angled portion 18 of the needle-through lumen 16 is typically located proximal to the rounded distal end face 14, which allows a shallower angle to a tissue-contacting surface of the rounded tip than if the needle-through lumen angled portion 18 only extended in the distal tip member 26

As best illustrated in FIG. 2, in the illustrated embodiment, the needle-through lumen 16 is defined by a first inner tubular member 22 which extends from the proximal to the distal end of the shaft 11. A deflection member such as a tendon wire 29 which extends in the shaft is configured to cause the distal shaft section to deflect as the tendon wire 29 is pulled proximally, and the tendon wire 29 is in the lumen of a second inner tubular member 23 in the illustrated embodiment. For ease of illustration, the second inner tubular member 23 is shown not in longitudinal cross section in FIG. 2. To effectively deflect the distal shaft section, the tendon wire 29 is preferably near the surface of the shaft in the deflecting (curving) section. The tendon wire 29 is fixedly secured relative to the shaft by bonding the distal end of the tendon wire within the distal shaft section (e.g., to distal tip member 26 discussed below). Although preferably a deflectable catheter, the catheter of the invention can have a variety of suitable catheter shaft configurations including non-deflecting configurations. In the embodiment illustrated in FIG. 2, a polymeric stabilizing member 24 is in the deflectable distal shaft section encasing the first and second inner tubular members 22, 23, however the shaft 11 can have a variety of suitable configurations, typically involving multiple tubular members joined end to end or forming multiple layers of the shaft 11. Details regarding construction of shafts of deflectable distal shaft section needle catheters, suitable for being used to form a catheter in accordance with the invention, can be found in U.S. patent application Ser. No. 10/676,616, incorporated by reference herein in its entirety. At the distal end of the polymeric stabilizing tubular member 24, filling material 25 is generally indicated which is typically polymeric or metallic tubular members or extensions thereof which in whole or in part fill the interior space of that portion of the shaft. A distal tip member 26 has a proximal end bonded to the distal end of a proximally adjacent tubular member 27 of the shaft 11. Although the distal tip member 26 is illustrated as a relatively short member butt-joined to the distal end of a tubular member of the shaft, a variety of suitable distal tip member configuration can be used for a catheter of the invention. For example, the distal tip member can be lap-joined to the proximally adjacent section of the shaft, and/or have a stem proximally extending into the proximally adjacent section of the shaft (e.g., forming part of the filling material 25). In embodiments having a distal tip member, the proximal end of the angled section 18 is typically located proximal to the distal tip member 26 proximal end as, for example, in the embodiment illustrated in FIG. 2, or is radially aligned with the distal tip member 26 proximal end. In a presently preferred embodiment, the distal tip member 26 is a polymeric member and is formed of a polymeric material having a relatively low Shore durometer hardness, lower than a polymeric material forming the proximally adjacent section of the shaft 11, to thereby provide a relatively soft, atraumatic distal end which minimizes injury to the patient's anatomy during advancement of the catheter 10 in the patient.

A proximal adapter 30 mounted to the proximal end of the shaft 11 controls the shaft deflection, needle extension length and needle position, and provides operative connectors such as the connector 31 configured for connecting to a fluid delivery or vacuum source and having port 32 providing access to the needle 12 for delivery of an agent, or for aspiration, through the lumen 19 of the needle 12. A variety of operative connectors may be provided at the proximal adapter 30 depending on the desired use of the catheter 10. In the illustrated embodiment, a second connector 33, similar to connector 31, is configured for connecting to a fluid delivery source and is in fluid communication with the needle-through lumen 16, so that the lumen 16 can be flushed to prevent clotted blood from bonding to the outer surface of the needle and the inner surface of the shaft which otherwise can inhibit movement of the needle 12 in the lumen 16. A deflection control mechanism 34 at the proximal adapter 30 is connected to the tendon wire 29 for deflecting the distal end of the catheter. To deliver an agent to a desired treatment location, the catheter is advanced through the patient's tortuous vasculature to the desired treatment location in a body cavity of the patient, such as a chamber of the patient's heart, the needle 12 is extended from the needle-through lumen 16 and into a wall of the body cavity at the treatment location, and an agent from an agent source (not shown) connected to connector 31 is infused from the needle 12 into the body cavity wall, and the needle 12 is then retracted back into the catheter 10 and the catheter repositioned or removed from the patient's body lumen.

Figure 3:
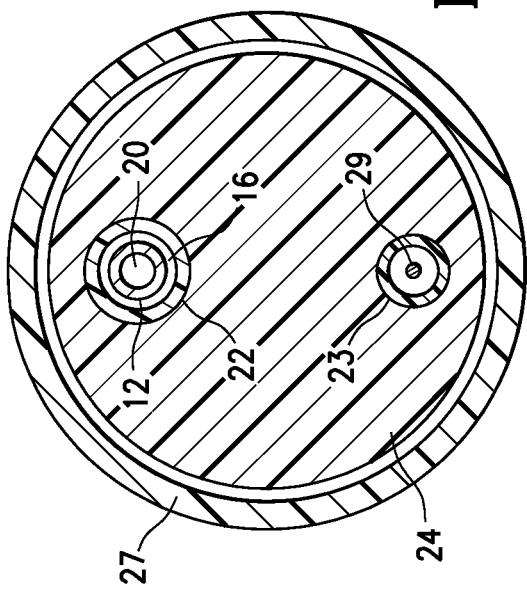

FIGS. 3 and 4 illustrate transverse cross sections of FIG. 2, taken along lines 3-3 and 4-4, respectively. In the embodiment of FIG. 2, the needle-through lumen 16 is eccentrically located in the shaft at least along the axially aligned portion 17 of the distal shaft section, and typically along the entire length extending proximally from the angled portion 18 to the proximal end of the lumen 16. However, the axially aligned portion 17 can alternatively be coaxially located in the shaft along all or part of the length proximal to the angled portion 18. In the embodiment of FIG. 2, the needle-through lumen 16 is typically axially aligned along the entire length proximal to the angled portion 18 to the proximal end of the shaft 11. However, the needle-through lumen 16 can have a variety of suitable alternative configurations such as a helical spiral-like configuration.

Figure 5:
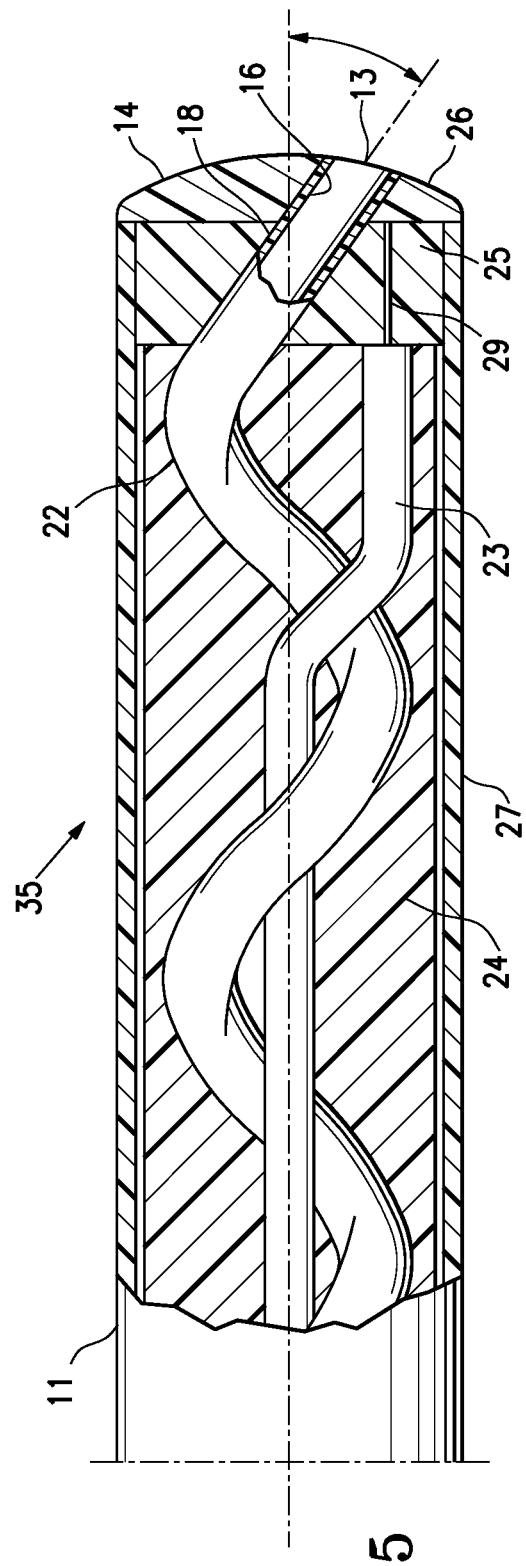
FIG. 5 illustrates the distal shaft section of an alternative embodiment of a catheter embodying features of the invention, in which the needle-through lumen extends helically to the needle-through port.

FIG. 5 illustrates the distal end of an alternative embodiment of a needle catheter 35 embodying features of the invention, similar to the needle catheter 10 of FIG. 1, except that the needle-through lumen 16 extends helically at least along a distal section of the shaft 11 to thereby direct the needle to exit from the catheter at an angle from the distal end face 14 in accordance with the invention. In the illustrated embodiment, the helically extending needle-through lumen 16 spirals around a section of the second inner tubular member 23 (defining the tendon wire 29 lumen) coaxially located in the shaft, although it could alternatively extend helically alongside the second inner tubular member 23, and the second inner tubular member 23 could alternatively be eccentrically, not coaxially, located in the shaft as in the embodiment of FIG. 2. Coaxial lumen(s) may be preferred in one embodiment at least in part due to the improved torque response provided to the catheter. The angled distal portion 18 is formed by the distal end of the helically extending needle-through lumen 16 (i.e., the needle is directed out of the catheter 35 at the vector aligning with the axis of the helical lumen 16 at the location of the port 13). Although illustrated in FIG. 5 extending helically around a full revolution or turn (360 degrees around the shaft), it should be understood that the helical distal angled portion 18 of the needle-through lumen 16 could alternatively be configured to extend helically along only a portion of the shaft to the needle-through port 13 (i.e., less than a full 360 degree turn in the shaft) to direct the needle to exit from the catheter at an angle. Thus, the helical angled distal portion 18 could transition proximally to an axially aligned section, similar to the embodiment of FIG. 2, which would provide for minimized friction during sliding of the needle 12 in the needle-through lumen 16. In one embodiment of a needle-through lumen 16 which transitions from an axially aligned proximal portion to a helical distal portion, the relatively short distal helical portion has a length of about 1 to about 10 cm. Alternatively, to provide for a more equally weighted catheter, the needle-through lumen 16 can extend helically proximally from the angled distal portion 18 along a substantial part, or all, of its length. The helically extending lumen 16 can extend at a constant angle or alternatively have a variable pitch. Although illustrated with the same stabilizing member 24, filling material 25, distal tip member 26 and shaft tubular member 27 as in the embodiment in FIG. 2, it should be understood that different shaft configurations can be useful with the helically extending needle-through lumen 16. The terminology "helically" as used herein should be understood to refer generally to a spiraling configuration, as opposed to an axially aligned member which extends substantially straight (i.e., with no intentionally induced spiraling or curving around the catheter longitudinal axis).

The distal end face 14 of the catheter 10, 35 is at least in part substantially perpendicular to a longitudinal axis of a distal section of the shaft (i.e., in a plane 90 degrees+/−about 30 degrees to about 45 degrees) to provide for stable positioning against the patient's body cavity wall without risking slippage, and the distal end face 14 and the needle-through lumen port 13 therein are configured to be pushed against the patient's body cavity wall. The catheter is configured to facilitate positioning the port 13 at a desired injection site, and unlike a port in a sidewall of the shaft proximal to the distal end face 14, the face 14 and port 13 in the distal end face can be affectively pushed against a wall of the patient's body cavity while the distal shaft section is perpendicular to the wall (e.g., myocardium) by pushing distally on the proximal end of the catheter such that the axial push force is transmitted through the catheter to it's distal tip. It should be noted that because the distal shaft section is deflectable, the distal end face 14 is substantially perpendicular to the longitudinal axis of the distal shaft section in the deflected configuration, and to the longitudinal axis of the entire length of the shaft in the non-deflected (relaxed) configuration. Typically, the distal end face 14 of the catheter has a curved surface configured to minimize trauma to the patient's anatomy as the catheter is advanced therein and pushed against the tissue at an injection site. In the illustrated embodiment, the distal end face 14 has a relatively large radius of curvature (i.e., relatively less sharply curved), and as a result the port 13 is substantially perpendicular to the longitudinal axis of the shaft. In the illustrated embodiment, the polymeric distal tip member 30 distal end forms the distal end face of the shaft.

The needle-through lumen 16 typically has a substantially uniform diameter (i.e., its diameter is the same along its entire length), and can slidably receive a straight needle or a preshaped bent needle therein. For example, a preshaped bent needle may have a bend corresponding to the bend at the junction of the axially aligned portion 17 and angled portion 18 of the needle-through lumen 16 of the embodiment of FIG. 2. Thus, an embodiment of the catheter having a preshaped bent needle does not change the angle at which the needle emerges from the port 13 (i.e., the prebent needle emerges at the same angle as a straight needle), but rather allows the bent needle to come to rest in the needle-through lumen at a predetermined extension length corresponding the length of the needle distal to the bend in the needle. The needle is typically formed of a nickel-titanium (NiTi) alloy to facilitate having the needle bend in the junction between the axially aligned and angled portions 17, 18 of the needle-through lumen 16, although a variety of suitable needles can be used including needles formed in whole or in part of stainless steel, or cobalt chromium, or other such alloys.

In accordance with the invention, the angled portion 18 of the needle-through lumen 16 extends to the needle-through port 13 at an angle greater than 0 degrees and less than 90 degrees relative to the longitudinal axis of the distal shaft section (or relative to the longitudinal axis of the non-deflected shaft). More specifically, the exit angle of the distal angled/curved portion 18 is preferably about 30 to about 60 degrees. In the embodiment illustrated in FIG. 2, the angled portion 18 extends at an angle of about 45 degrees relative to the longitudinal axis of the distal shaft section. The angled portion 18 typically has a length of about 1 to about 20 mm, or typically a relatively small percentage of the total length of the needle-through lumen 16. The catheter total length varies, and in one embodiment it may be about 105 to about 115 cm.

In a method of delivering an agent to an injection site in a wall of a patient's body cavity, a catheter of the invention is introduced within a patient's vasculature with the needle in the retracted configuration and the distal shaft section in the relaxed (non-deflected) configuration. Specifically, the piercing distal tip of the needle in the retracted configuration is typically located in the axially aligned portion 17 of the needle-through lumen 16 in the embodiment of FIG. 2, which improves the flexibility of the distal tip of the catheter during percutaneous advancement of the catheter to a desired location in the patient's body cavity. For example, in a presently preferred embodiment, the catheter is advanced into the left ventricle of the patient's heart for injecting an agent such as a biomaterial (cells) into the myocardium of the heart.

Figure 6:
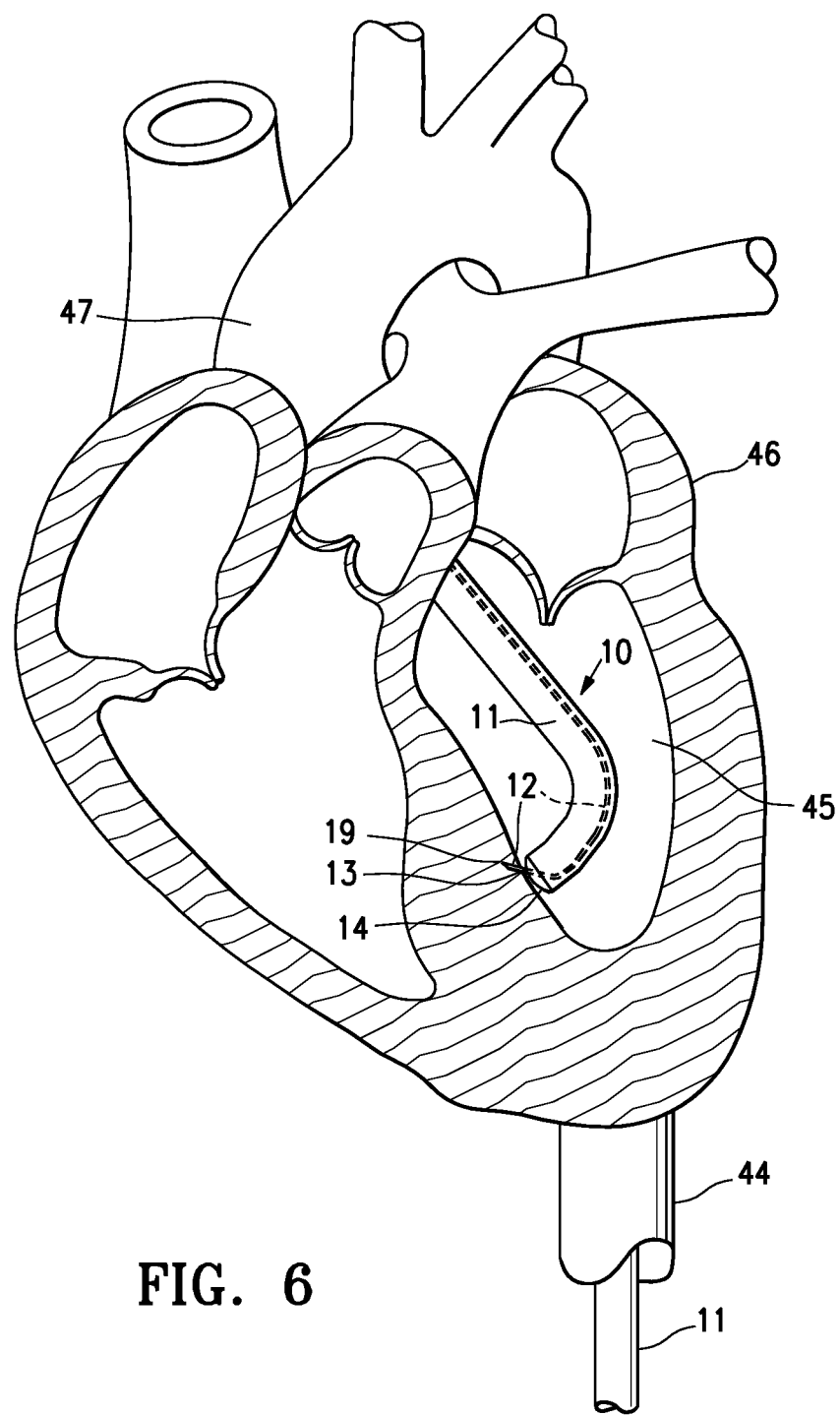
FIG. 6 illustrates the catheter of FIG. 1 within a left ventricle of a patient's heart during an agent injection medical procedure.

FIG. 6 illustrates a needle catheter of the invention with the distal end of the catheter within the left ventricle 45 of the patient's heart 46. The catheter is typically advanced in a retrograde fashion within the aorta 47, via the lumen of an introducer sheath which is inserted into the femoral artery. The catheter in the illustrated embodiments is not configured for advancement over a guidewire, although in alternative embodiments and delivery sites a guidewire lumen is provided in the shaft 11 for slidably receiving a guidewire therein. The catheter may be inserted into position using a guiding catheter 44 that is first inserted into the introducer sheath. In the preferred intracardiac application, a deflecting mechanism is desired. By activating the deflection member (e.g., tendon wire 29) using the deflection control mechanism 34 the distal end of the catheter is caused to deflect away from the longitudinal axis of the shaft 11 toward the desired injection site on the wall of the heart, e.g., as illustrated in FIG. 6.

The method includes pushing the distal end face 14 against the patient's body cavity wall at the injection site. In the illustrated embodiment, although the distal end face 14 is rounded, the port 13 of catheter is configured to thereby be pushed against the heart wall. With the face 14 against the wall, the method includes advancing the needle to an extended configuration in which the piercing distal tip 19 of the needle extends distally out the port 13, such that the needle 12 extends into the body cavity wall at the angle of the angled portion 18 of the needle-through lumen 16 and thereby forms an angled injection pathway in the patient's body cavity wall. FIG. 6 illustrates the needle 12 in the extended configuration with the piercing distal tip 19 in the heart wall (the part of the needle 12 within the needle-through lumen is illustrated in phantom in FIG. 6). At the proximal end of the angled portion 18, the needle-through lumen 16 is preferably configured to facilitate slidably advancing the needle toward the port 13. For example, during advancement of the needle 12 from the retracted configuration illustrated in FIG. 2 to the extended configuration of FIG. 6, the distal piercing tip 19 of the needle 12 contacts the wall of the angled portion 18 which has a ramp-like shape angled toward the needle-through port 13 and which defines the needle-through lumen 16. Reinforced walls or added ramps at the distal end of the axially aligned portion 17 of the needle-through lumen 16 can also be used to facilitate advancing the needle 12 into the angled portion 18. Thus, as the needle is distally advanced in the needle-through lumen 16, it is thereby directed into the angled portion 18 of the needle-through lumen 16.

Because the distal shaft section is oriented substantially perpendicular to the desired injection site during advancement of the needle 12, push force is transmitted axially from the proximal to the distal end of the catheter and thereby pushes the distal end face 14 and port 13 against the heart wall. The method of the invention includes causing agent from an agent source (not shown), which is connected to connector 31 to thereby be in fluid communication with the proximal end of the needle 12, to flow through the needle lumen 20, to thereby deliver the agent into the angled injection pathway in the patient's body cavity wall. Compared to a conventional straight-in injection pathway (i.e., normal to the heart wall surface), the angled injection pathway preferably provides for less expulsion of the delivered agent from the beating heart wall. The angled injection pathway has a longer length to a given injection depth in the heart wall than would a corresponding straight-in injection pathway to the same injection depth. Additionally, the needle 12 provides improved stabilization of the distal tip of the catheter against the beating heart wall due to the angle of the needle 12 in the heart wall. Unlike a catheter which has a non-angled needle-through lumen and which has a preshaped bent needle which is biased to assume a deflected/angled configuration as it's bent portion exits the non-angled needle-through lumen, the angled portion 18 of the needle-through lumen 16 of the catheter of the invention causes the needle to extend at an angle from the moment it exits the needle-through lumen and enters the tissue, and even while being potentially restrained from deflecting to a biased configuration by the surrounding body cavity wall into which it has been extended. The catheter design of the invention is configured to preferably keep the distal tip of the catheter against the heart wall during advancement of the needle 12 out the port 13 and thereafter during infusion of an agent from the needle 12 into the heart wall, for improved agent delivery.

The dimensions of catheter 10, 35 depend upon factors such as the catheter type and the size of the body lumen through which the catheter must pass. By way of example, the catheter outer diameter is typically made to be about 7-8 French compatible to about 10-11 French compatible. The needle is typically about a 25 gauge to a 31 gauge, more specifically about a 27 gauge needle. The overall length of the catheter 10 may range from about 100 to about 150 cm, and is typically about 110 cm.

A variety of suitable agents can be delivered using a catheter and method of the invention. The agents are typically intended for treatment and/or diagnosis of coronary, neurovascular, and/or other vascular disease, and may be useful as a primary treatment of the diseased anatomy, or alternatively, as a secondary treatment in conjunction with other interventional therapies such as angioplasty or stent delivery.

Suitable therapeutic agents include, but are not limited to, thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. In a presently preferred embodiment, the agent is a cell. In addition to therapeutic agents, a variety of diagnostic agents can be used according to the present invention. The agent may be provided in a variety of suitable formulations and carriers including liposomes, polymerosomes, nanoparticles, microparticles, lipid/polymer micelles, and complexes of agents with lipid and/or polymers, and the like.

Although discussed primarily in terms of an embodiment in which the distal tip of the catheter is a polymeric ataumatic tip member, it should be understood that a catheter of the invention can be configured for different uses and with a variety of suitable alternative designs. For example, in one embodiment, the distal tip member is an electrode typically having a metallic distal end face configured for diagnostic and/or therapeutic purposes, which is in electrical communication with an electrical connector (not shown) at the proximal end of the catheter. Other modifications and improvements can be made to the invention without departing from the scope thereof. Additionally, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. An agent delivery needle catheter configured for injecting an agent at an injection site in a wall of a patient's body cavity, comprising:
    a) an elongated catheter shaft having a proximal end, a distal end, and a needle-through lumen therein extending from the proximal end to a needle-through port in a distal end face of the catheter, and the distal end face is at least in part substantially perpendicular to a longitudinal axis of a distal section of the shaft such that the distal end face and needle-through lumen port therein are configured to be pushed against the wall of the patient's body cavity, and the needle-through lumen has an angled distal portion which extends to the needle-through port at an angle greater than 0 degrees and less than 90 degrees relative to the longitudinal axis; and
    b) a hollow needle slidably disposed in the needle-through lumen of the shaft, having a piercing distal tip and a lumen in fluid communication with a port in the piercing distal tip, and having a retracted configuration in which the piercing distal tip of the needle is in the needle-through lumen of the shaft, and an extended configuration in which the piercing distal tip extends distally out the needle-through port, such that the catheter is configured to form an angled injection pathway in the wall of the patient's body cavity by directing the needle into the wall of the patient's body cavity at the angle of the angled distal portion of the needle-through lumen with the distal end face against the wall of the patient's body cavity at the injection site.

2. The catheter of claim 1 wherein the distal end face is rounded.

3. The catheter of claim 2 wherein the shaft has a distal tip member having a distal end forming the rounded distal end face of the catheter, and a proximal end bonded to a distal end of a tubular member of the shaft, and the proximal end of the angled section of the needle-through lumen is radially aligned with or proximal to the distal tip member proximal end.

4. The catheter of claim 3 wherein the distal tip member is formed at least in part of a polymeric material having a lower Shore durometer hardness than a polymeric material forming the shaft tubular member bonded thereto.

5. The catheter of claim 1 wherein the needle-through lumen has an axially aligned portion located proximal to the angled distal portion.

6. The catheter of claim 5 wherein the axially aligned portion of the needle-through lumen is eccentrically located in the shaft, and the angled portion extends across the longitudinal axis of the shaft.

7. The catheter of claim 1 wherein the needle-through lumen extends axially aligned and eccentrically located in the shaft from the angled portion to the proximal end of the needle-through lumen.

8. The catheter of claim 1 wherein the angled portion extends helically along at least a portion of the shaft.

9. The catheter of claim 1 wherein the needle-through lumen is the single lumen of the shaft open to outside of the catheter in the distal shaft section, and the needle-through port is the single port in the distal tip section of the shaft.

10. The catheter of claim 1 wherein the needle-through lumen has a substantially uniform diameter.

11. The catheter of claim 1 wherein the angled portion extends at an angle of about 30 to about 60 degrees relative to the longitudinal axis.

12. A method of delivering an agent to an injection site in a wall of a patient's body cavity, comprising:
    a) introducing within the patient's vasculature a catheter comprising an elongated catheter shaft having a proximal end, a distal end, and a needle-through lumen extending from the proximal end to a needle-through port in a distal end face of the catheter, and the distal end face is at least in part substantially perpendicular to a longitudinal axis of a distal section of the shaft such that the distal end face and needle-through lumen port therein are configured to be pushed against the wall of the patient's body cavity, and the needle-through lumen has an angled distal portion which extends to the needle-through port at an angle greater than 0 degrees and less than 90 degrees relative to the longitudinal axis, and a hollow needle slidably disposed in the needle-through lumen of the shaft having a piercing distal tip, a lumen in fluid communication with a port in the piercing distal tip, and a retracted configuration in which the piercing distal tip is within the needle-through lumen of the catheter shaft, and percutaneously advancing the introduced catheter with the needle in the retracted configuration to position the distal end of the catheter in the patient's body cavity;
    b) pushing the distal end face against the patient's body cavity wall at the injection site, and advancing the needle to an extended configuration in which the piercing distal tip of the needle extends distally out the port with the distal end face against the body cavity wall, such that the needle extends into the body cavity wall at the angle of the angled portion of the needle-through lumen and thereby forms an angled injection pathway in the patient's body cavity wall; and
    c) causing agent from an agent source in fluid communication with the proximal end of the needle to flow through the needle lumen, to thereby deliver the agent into the angled injection pathway in the patient's body cavity wall.

13. The method of claim 12 wherein the needle-through lumen includes an axially aligned portion located proximal to the angled distal portion, and b) includes slidably advancing the piercing distal tip of the needle through a lumen bend to the extended configuration.

14. The method of claim 12 wherein the distal end face is rounded, and the port is pushed against the wall of the patient's body cavity in b).

15. The method of claim 12 wherein the piercing distal tip of the needle contacts a wall which has a ramp-shape angled toward the needle-through port and which defines the needle-through lumen as the needle is distally advanced in the needle-through lumen, and is thereby directed into the angled portion of the needle-through lumen in b).

16. The method of claim 12 wherein the shaft distal shaft section is oriented substantially perpendicular to the injection site during b) and c), such that push force transmitted axially to the distal end of the catheter pushes the distal end face and port against the wall in b).

17. The method of claim 12 wherein the agent is a biomaterial comprising cells and the body cavity is a chamber of the patient's heart, and the needle piercing distal tip is advanced into the myocardium of the patient's heart wall in b) for agent delivery into the myocardium in c).

* * * * *